(12) United States Patent
Kung et al.

(10) Patent No.: US 9,012,665 B2
(45) Date of Patent: Apr. 21, 2015

(54) AMORPHOUS CABAZITAXEL

(71) Applicant: Yung Shin Pharm. Ind. Co., Ltd., Tachia, Taichung (TW)

(72) Inventors: Liang-Rern Kung, Hsinchu (TW); Yi-Ting Hung, Tainan (TW); Tung-Shen Fang, Taichung (TW); Po-Wei Chang, Taichung (TW); Tsang-Miao Huang, Changhua (TW)

(73) Assignee: Yung Shin Pharm. Ind. Co., Ltd., Tachia, Taichung (TW)

( * ) Notice: Subject to any disclaimer, the term of this patent is extended or adjusted under 35 U.S.C. 154(b) by 31 days.

(21) Appl. No.: 13/952,117

(22) Filed: Jul. 26, 2013

(65) Prior Publication Data

US 2014/0228426 A1     Aug. 14, 2014

Related U.S. Application Data

(60) Provisional application No. 61/677,991, filed on Jul. 31, 2012.

(51) Int. Cl.
  *C07D 407/00* (2006.01)
  *C07D 305/14* (2006.01)
  *A61K 31/337* (2006.01)

(52) U.S. Cl.
  CPC ............ *C07D 305/14* (2013.01); *A61K 31/337* (2013.01)

(58) Field of Classification Search
  CPC .................................................... C07D 305/14
  USPC ........................................................ 549/510
  See application file for complete search history.

(56) References Cited

U.S. PATENT DOCUMENTS

| | | | |
|---|---|---|---|
| 8,476,310 B2 * | 7/2013 | Palepu | ........................... 514/449 |
| 2005/0065138 A1 | 3/2005 | Didier | |
| 2008/0306137 A1 | 12/2008 | Hao | |
| 2009/0118354 A1 | 5/2009 | Liu et al. | |
| 2011/0152360 A1 | 6/2011 | Liu et al. | |
| 2012/0065255 A1 | 3/2012 | Palepu | |
| 2012/0149925 A1 | 6/2012 | Kung et al. | |
| 2013/0109870 A1 * | 5/2013 | Lahiri et al. | ................... 549/510 |
| 2014/0011865 A1 | 1/2014 | Simo et al. | |

FOREIGN PATENT DOCUMENTS

| | | |
|---|---|---|
| WO | WO 2007/020085 | 2/2007 |
| WO | WO 2011/051894 | 9/2009 |
| WO | WO 2009/115655 | 5/2011 |
| WO | WO 2013/024495 | 2/2013 |

OTHER PUBLICATIONS

International Search Report and Written Opinion of International Patent Application PCT/US2013/052366 with a mailing date of Nov. 28, 2013.

* cited by examiner

*Primary Examiner* — Noble Jarrell
*Assistant Examiner* — Raymond Covington
(74) *Attorney, Agent, or Firm* — Perkins Coie LLP; Viola T. Kung

(57) ABSTRACT

The present invention is directed to an amorphous form of cabazitaxel, which can be prepared by dissolving a solid form of cabazitaxel in an organic solvent, and removing the organic solvent to dryness. The amorphous form of cabazitaxel is characterized by DSC as in FIG. 1 and/or X-ray powder diffraction pattern as in FIG. 2.

10 Claims, 3 Drawing Sheets

AMORPHOUS CABAZITAXEL

The present application claims priority to U.S. Provisional Application No. 61/677,991, filed on Jul. 31, 2012, which is incorporated herein by reference in its entirety.

FIELD OF THE INVENTION

The present disclosure relates to amorphous cabazitaxel and process of preparing it.

BACKGROUND OF THE INVENTION

Taxoids are compounds derived from taxol (also referred to as paclitaxel), an isolated natural product and an important anticancer drug. Taxoids stabilize microtubules during mitosis to treat patients with different kinds of cancer (e.g. ovarian cancer, breast cancer and lung cancer).

Cabazitaxel is a semi-synthetic derivative of a natural taxoid 10-deacetylbaccatin III (10-DAB)) with potential antineoplastic activity. Cabazitaxel binds to and stabilizes tubulin, resulting in the inhibition of microtubule depolymerization and cell division, cell cycle arrest in the G2/M phase, and the inhibition of tumor cell proliferation. Unlike other taxane compounds, this agent is a poor substrate for the membrane-associated, multidrug resistance, P-glycoprotein (P-gp) efflux pump and may be useful for treating multidrug-resistant tumors. In addition, cabazitaxel penetrates the blood-brain barrier.

Cabazitaxel was developed by Sanofi-Aventis and was approved by FDA in 2010. JEVTANA® (cabazitaxel injection) is a microtubule inhibitor indicated in combination with prednisone for the treatment of patients with hormone-refractory metastatic prostate cancer previously treated with a docetaxel-containing treatment regimen.

The systematic (IUPAC) name of cabazitaxel is (1S,2S,3R,4S,7R,9S,10S,12R,15S)-4-(acetyloxy)-15-{[(2R,3S)-3-{[(tert-butoxy)carbonyl]amino}-2-hydroxy-3-phenylpropanoyl]oxy}-1-hydroxy-9,12-dimethoxy-10,14,17,17-tetramethyl-11-oxo-6-oxatetracyclo[11.3.1.03,10.04,7]heptadec-13-en-2-yl benzoate. Its chemical structure is shown below.

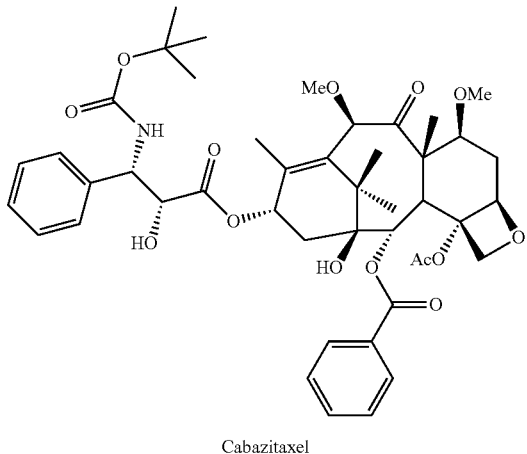

Cabazitaxel

DETAILED DESCRIPTION OF THE INVENTION

Figure 1:
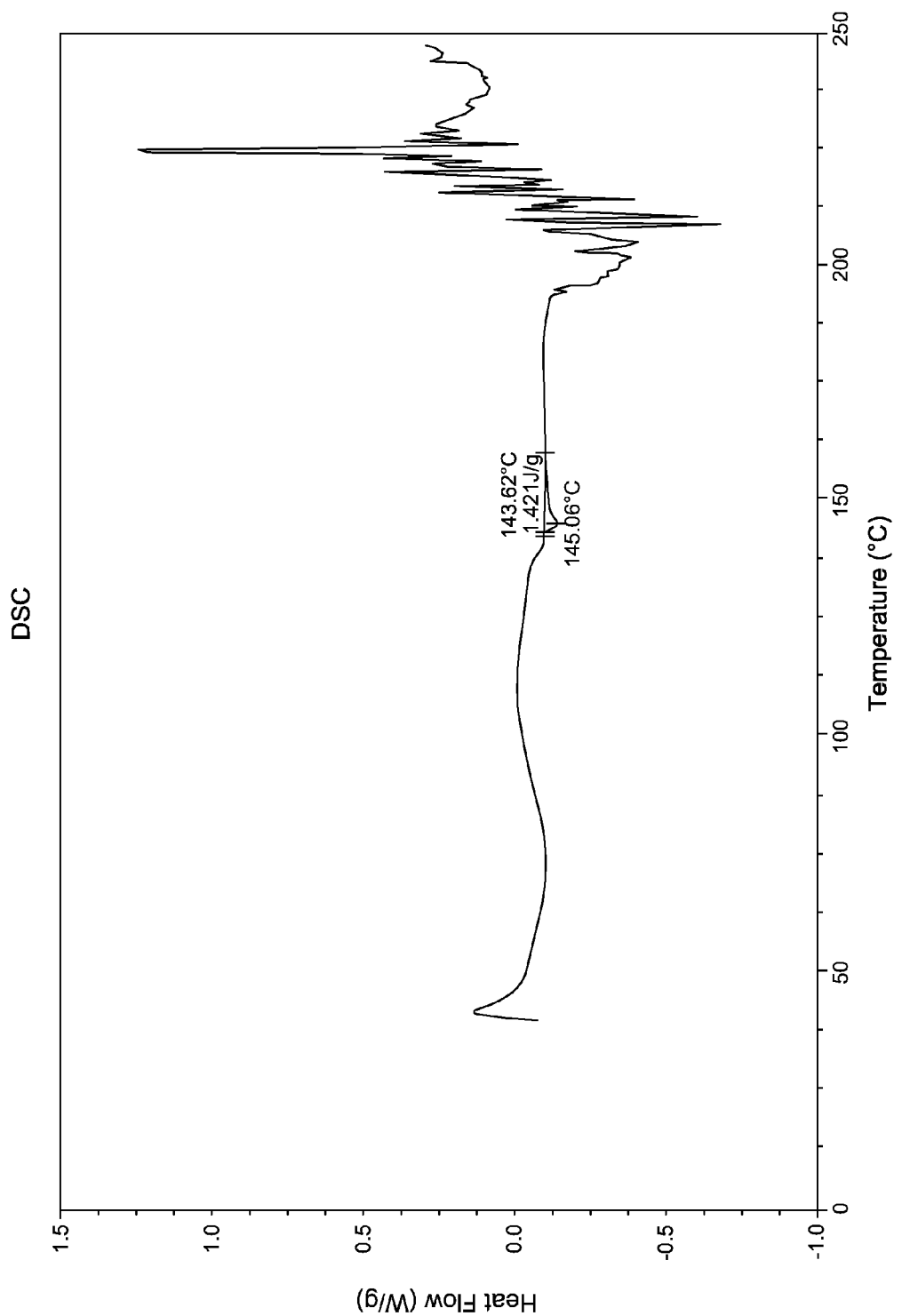
FIG. 1 shows a thermogram of differential scanning calorimetry (DSC) spectrum of amorphous cabazitaxel (Example 19).

The present invention is directed to an amorphous form of cabazitaxel, which can be prepared by dissolving a solid form, e.g., a crystalline form, of cabazitaxel in an organic solvent, and removing the organic solvent to dryness.

An amorphous form, as used herein, refers to a solid without a shape. An amorphous solid is a solid that lacks the long-range order characteristic of a crystal. An amorphous solid is disordered and it does not have a single repeat unit like a crystal.

Method of Preparing an Amorphous Form of Cabazitaxel

Crystalline forms of cabazitaxel can be purchased from several commercial sources, e.g., MedKoo Biosciences. Alternatively, a crystalline form of cabazitaxel can be prepared according to US2012/0149925, which is incorporated herein by reference in its entirety.

An amorphous form cabazitaxel can be prepared by a method comprising (a) dissolving a solid form of cabazitaxel in an organic solvent or a solvent mixture, and (b) removing the organic solvent or the solvent mixture to form the compound. Organic solvents suitable for this invention include $C_{1-4}$ halogenated hydrocarbon, $C_{1-4}$ alcohols, $C_{3-5}$ ketone, $C_{1-4}$ nitrile, $C_{2-8}$ ether, or $C_{3-7}$ ester. A suitable organic solvent or solvent mixture for example is dichloromethane, ethanol, methanol, acetone, acetonitrile, ethyl acetate, isopropyl acetate, isopropyl alcohol, diispropyl ether, diethyl ether, tetrahydrofuran, 1,2-dimethoxyethane, toluene, chloroform, dimethylformamide, dimethylsulfoxide, or a combination thereof.

The solvent or solvent mixture of the above method can be removed by evaporation, vacuum condensation, spray drying, or filtration and drying. In one embodiment, the solvent or solvent mixture is removed, for example, by vacuum condensation, at about 25-60° C., or about 25-45° C., and under a pressure is less than about 700 mm Hg, preferably less than about 300 or 100 mmHg. In another embodiment, the solvent or solvent mixture is removed by spray drying with nitrogen gas having an inlet temperature of about 50-150° C. In another embodiment, the solvent or solvent mixture is removed by drying under reduced pressure at about 40° C. The process of removing the solvent in general takes place quickly to avoid orderly crystal growth, in about 1-60 minutes, or 3-30 minutes, or 5-10 minutes.

The amorphous cabazitaxel can optionally be re-purified by re-dissolving the solid in a suitable organic solvent as describe above, followed by removing the solvent to dryness.

Characterization of Amorphous Cabazitaxel

The amorphous cabazitaxel can be characterized by the following analysis.

Thermal analysis: Two thermal analysis, thermogravimetric analysis (TGA) and differential scanning calorimetry (DSC) can be used. TGA measures the change in the mass of sample as the temperature is changed. The profile of the overall thermogravimetric weight loss versus temperature curve provides reliable indication of the phase and weight changes of the pharmaceutical compounds.

DSC examines the changes in physical properties of the pharmaceutical compound with temperature or time. During operation, DSC heats the test sample, measures heat flow between the test sample and its surrounding environment, and records a test thermogram of the test sample based on the measured heat flow. DSC provides information regarding the onset temperature, the endothermal maximum of melting, and the enthalpy of the compound.

Powder X-ray diffraction (PXRD): PXRD is used to characterize the solid state character of a compound.

High Performance Liquid Chromatography (HPLC): The content and/or purity of the amorphous cabazitaxel can be determined by HPLC method.

UV Spectroscopy: The UV spectroscopy can be used to perform qualitative analysis of the amorphous cabazitaxel.

Infrared (IR) Spectroscopy: Functional groups of the amorphous cabazitaxel can be determined by IR spectra based on their respective light transmittance.

Pharmaceutical Formulation

The present invention is directed to a pharmaceutical formulation comprising amorphous cabazitaxel and a pharmaceutically acceptable carrier. The pharmaceutical acceptable carriers are in general those commonly used and generally recognized by person skilled in the art of pharmaceutical formulation.

EXAMPLES

As used herein, "DMF" means dimethylformamide; "10-DAB" means 10-deacetylbaccatin III; "THF" means tetrahydrofuran.

Example 1

Preparation of 7,10-di-methoxy-10-deacetylbaccatin (III) (C1) Catalyzed by CsBr

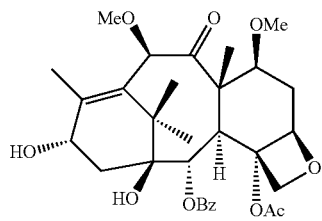

C1

A solution of sodium hydride (60%, 3 eq, 0.22 g)/CsBr (0.5 eq, 0.20 g) was dissolved in co-solvent THF/DMF (2/1, 6 mL), cooled down to −20° C. under nitrogen, and stirred for 20 minutes. Natural taxoid 10-deacetylbaccatin III (10-DAB) was obtained from Yung Shin Pharm. Ind. Co. LTD. (Taichung, Taiwan) or SM Herbal (India). 10-DAB (1 eq, 1 g)/Me$_2$SO$_4$ (10 eq, 1.74 mL) in THF/DMF (2/1, 6 mL) was added into the sodium hydride reaction mixture slowly. The reaction mixture was allowed to warm up to room temperature gradually. The reaction mixture was stirred for 2 hours until the reaction was completed. The mixture was quenched with 10% AcOH/THF, and extracted with CH$_2$Cl$_2$ and water. After partition, the organic layer extracted with saturated NaHCO$_{3(aq)}$. It was concentrated and purification by recrystallization (CH$_2$Cl$_2$/Hexane) to yielded C1 as white solid (yield: 50%, 0.37 g, LC purity: 90%). $^1$H NMR (400 MHz, D$^6$-DMSO) δ 8.01 (d, J=7.2 Hz, 2H), 7.66 (t, J=7.4 Hz, 1H), 7.56 (t, J=7.6 Hz, 2H), 5.37 (d, J=7.2 Hz, 1H), 5.31 (d, J=4.0 Hz, 1H), 4.97 (d, J=8.4 Hz, 1H), 4.74 (s, 1H), 4.72-4.61 (m, 1H), 4.40 (s, 1H), 4.03 (dd, J=8.2, 13.4 Hz, 2H), 3.81 (dd, J=6.6, 10.6 Hz, 1H), 3.75 (d, J=7.2 Hz, 1H), 3.29 (s, 3H), 3.21 (s, 3H), 2.74-2.62 (m, 1H), 2.20 (s, 3H), 2.17 (d, J=8.4 Hz, 2H), 1.97 (s, 3H), 1.58-1.41 (m, 4H), 0.93 (s, 6H); $^{13}$C NMR (100 MHz, D$^6$-DMSO) δ 205.5, 169.7, 165.2, 144.1, 133.3, 132.8, 130.2, 129.5, 128.7, 83.3, 82.8, 80.5, 80.1, 76.9, 75.3, 74.4, 66.2, 56.7, 56.5, 56.1, 47.1, 42.5, 31.8, 26.9, 22.4, 20.5, 15.2, 10.1.

Example 2

Preparation of 7,10-di-methoxy-10-deacetylbaccatin (III) (C1) Catalyzed by CsBr

A solution of sodium hydride (60%, 3 eq, 0.22 g)/CsBr (0.5 eq, 0.20 g) was dissolved in co-solvent THF/DMF (2/1, 6 mL), cooled down to −20° C. under nitrogen and was stirred for 20 minutes. 10-DAB (1 eq, 1 g)/MeI (10 eq, 1.2 mL) in THF/DMF (2/1, 6 mL) was added into the sodium hydride reaction mixture slowly. The reaction mixture was allowed to warm up to room temperature gradually. The reaction mixture was stirred for 2 hours until the reaction was completed. The mixture was quenched with 10% AcOH/THF, and extracted with CH$_2$Cl$_2$ and water. After partition, the organic layer extracted with saturated NaHCO$_{3(aq)}$. It was concentrated and purification by recrystallization (CH$_2$Cl$_2$/Hexane) to yielded C1 as white solid (LC purity: 52%)

Example 3

Preparation of 7,10-di-methoxy-10-deacetylbaccatin (III) (C1) Catalyzed by CsBr

A solution of sodium hydride (60%, 3 eq, 0.22 g)/CsBr (0.5 eq, 0.20 g) was dissolved in co-solvent THF/DMF (2/1, 6 mL), cooled down to −20° C. under nitrogen and was stirred for 20 minutes. 10-DAB (1 eq, 1 g)/MePhSO$_3$Me (10 eq, 2.77 mL) in THF/DMF (2/1, 6 mL) was added into the sodium hydride reaction mixture slowly. The reaction mixture was allowed to warm up to room temperature gradually. The reaction mixture was stirred for 2 hours until the reaction was completed. The mixture was quenched with 10% AcOH/THF, and extracted with CH$_2$Cl$_2$ and water. After partition, the organic layer extracted with saturated NaHCO$_{3(aq)}$. It was concentrated and purification by recrystallization (CH$_2$Cl$_2$/Hexane) to yielded C1 as white solid (LC purity: 40%)

Example 4

Preparation of 7,10-di-methoxy-10-deacetylbaccatin (III) (C1) Catalyzed by CsBr

A solution of sodium hydride (60%, 3 eq, 0.22 g)/CsBr (0.5 eq, 0.20 g) was dissolved in co-solvent THF/DMF (2/1, 6 mL), cooled down to −20° C. under nitrogen and was stirred for 20 minutes. 10-DAB (1 eq, 1 g)/CF$_3$SO$_3$Me (10 eq, 2.08 mL) in THF/DMF (2/1, 6 mL) was added into the sodium hydride reaction mixture slowly. The reaction mixture was allowed to warm up to room temperature gradually. The reaction mixture was stirred for 2 hours until the reaction was completed. The mixture was quenched with 10% AcOH/THF, and extracted with CH$_2$Cl$_2$ and water. After partition, the organic layer extracted with saturated NaHCO$_{3(aq)}$. It was concentrated and purification by recrystallization (CH$_2$Cl$_2$/Hexane) to yielded C1 as white solid (LC purity: 46%)

Example 5

Preparation of 7,10-di-methoxy-10-deacetylbaccatin (III) (C1) Catalyzed by a Mixture of CsBr and KBr A solution of sodium hydride (60%, 3 eq, 0.22 g)/CsBr (0.5 eq, 0.20 g)/KBr (0.1 eq, 0.02 g) was dissolved in co-solvent THF/DMF (2/1, 6 mL), cooled down to −20° C. under nitrogen and was stirred 20 minutes. 10-DAB (1 eq, 1 g)/Me$_2$SO$_4$ (10 eq, 1.74 mL) in THF/DMF (2/1, 6 mL) was added into the sodium hydride reaction mixture slowly. The reaction mixture was allowed to warm up to room temperature gradually. The reaction mixture was stirred for 2 hours until the reaction was completed. The mixture was quenched with 10% AcOH/THF, and extracted with CH$_2$Cl$_2$ and water. After partition, the organic layer extracted with saturated NaHCO$_{3(aq)}$. It was concentrated and purification by recrystallization (CH$_2$Cl$_2$/Hexane) to yielded C1 as white solid (LC purity: 66%)

Example 6

Preparation of 7,10-di-methoxy-10-deacetylbaccatin (III) (C1) Catalyzed by a Mixture of CsBr and MgBr$_2$ A solution of sodium hydride (60%, 3 eq, 0.22 g)/CsBr (0.5 eq, 0.20 g)/MgBr$_2$ (0.1 eq, 0.03 g) was dissolved in co-solvent THF/DMF (2/1, 6 mL), cooled down to −20° C. under nitrogen, and stirred for 20 minutes. 10-DAB (1 eq, 1 g)/Me$_2$SO$_4$ (10 eq, 1.74 mL) in THF/DMF (2/1, 6 mL) was added into the sodium hydride reaction mixture slowly. The reaction mixture was allowed to warm up to room temperature gradually. The reaction mixture was stirred for 2 hours until the reaction was completed. The mixture was quenched with 10% AcOH/THF, and extracted with CH$_2$Cl$_2$ and water. After partition, the organic layer extracted with saturated NaHCO$_{3(aq)}$. It was concentrated and purification by recrystallization (CH$_2$Cl$_2$/Hexane) to yielded C1 as white solid (LC purity: 74%).

Example 7

Preparation of 7,10-di-methoxy-10-deacetylbaccatin (III) (C1) Catalyzed by a Mixture of CsBr and ZnBr$_2$ A solution of sodium hydride (60%, 3 eq, 0.22 g)/CsBr (0.5 eq, 0.20 g)/ZnBr$_2$ (0.1 eq, 0.04 g) was dissolved in co-solvent THF/DMF (2/1, 6 mL), cooled down to −20° C. under nitrogen, and stirred for 20 minutes. 10-DAB (1 eq, 1 g)/Me$_2$SO$_4$ (10 eq, 1.74 mL) in THF/DMF (2/1, 6 mL) was added into the sodium hydride reaction mixture slowly. The reaction mixture was allowed to warm up to room temperature gradually. The reaction mixture was stirred for 17 hours until the reaction was completed. The mixture was quenched with 10% AcOH/THF, and extracted with CH$_2$Cl$_2$ and water. After partition, the organic layer extracted with saturated NaHCO$_{3(aq)}$. It was concentrated and purification by recrystallization (CH$_2$Cl$_2$/Hexane) to yielded C1 as white solid (LC purity: 44%).

Example 8

Preparation of 7,10-di-methoxy-10-deacetylbaccatin (III) (C1) Catalyzed by a Mixture of CsBr and CeCl$_3$ A solution of sodium hydride (60%, 3 eq, 0.22 g)/CsBr (0.5 eq, 0.20 g)/CeCl$_3$ (0.1 eq, 0.05 g) was dissolved in co-solvent THF/DMF (2/1, 6 mL), cooled down to −20° C. under nitrogen, and stirred for 20 minutes. 10-DAB (1 eq, 1 g)/Me$_2$SO$_4$ (10 eq, 1.74 mL) in THF/DMF (2/1, 6 mL) was added into the sodium hydride reaction mixture slowly. The reaction mixture was allowed to warm up to room temperature gradually. The reaction mixture was stirred for 2 hours until the reaction was completed. The mixture was quenched with 10% AcOH/THF, and extracted with CH$_2$Cl$_2$ and water. After partition, the organic layer extracted with saturated NaHCO$_{3(aq)}$. It was concentrated and purification by recrystallization (CH$_2$Cl$_2$/Hexane) to yielded C1 as white solid (LC purity: 61%).

Example 9

Preparation of 7,10-di-methoxy-10-deacetylbaccatin (III) (C1) by (Naphthalene)$^-$.Li$^+$ and Catalyzed with CsBr Lithium (3.0 eq, 40 mg) and naphthalene (3.3 eq, 780 mg) in anhydrous THF (11 mL) was stirred under nitrogen at 25° C. for 16 hr, then cooled to −78° C. The solution of 10-DAB (1 eq, 1 g) and Me$_2$SO$_4$ (10 eq, 1.74 mL) in anhydrous THF (9 mL) was added into mixture of (Naphthalene)$^-$.Li$^+$ and CsBr (0.5 eq, 200 mg) slowly. The reaction mixture was returned gradually to room temperature. After stirred for 6.5 h, the starting material was consumed. The mixture was quenched by 10% AcOH/THF and then extracted with CH$_2$Cl$_2$ and H$_2$O. The organic layer was dried by rotavapor to obtain the crude C1 (HPLC purity: 22%). (*Tetrahedron*, 66, 871, 2010; *Tetrahedron lett.*, 39, 4183, 1998)

Example 10

Preparation of 7,10-di-methoxy-10-deacetylbaccatin (III) (C1) by (Naphthalene)$^-$.Li$^+$ and Catalyzed with KBr Lithium (3.0 eq, 40 mg) and naphthalene (3.3 eq, 780 mg) in anhydrous THF (11 mL) was stirred under nitrogen at 25° C. for 16 hr, then cooled to −78° C. The solution of 10-DAB (1 eq, 1 g) and Me$_2$SO$_4$ (10 eq, 1.74 mL) in anhydrous THF (9 mL) was added into mixture of (Naphthalene)$^-$.Li$^+$, and KBr (0.5 eq, 110 mg) slowly. The reaction mixture was returned gradually to room temperature. After stirred for 6.5 h, the starting material was consumed. The mixture was quenched by 10% AcOH/THF and then extracted with CH$_2$Cl$_2$ and H$_2$O. The organic layer was dried by rotavapor to obtain the crude C1 (HPLC purity: 10%). (*Tetrahedron*, 66, 871, 2010; *Tetrahedron lett.*, 39, 4183, 1998)

Example 11

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the Catalyst of LiBr

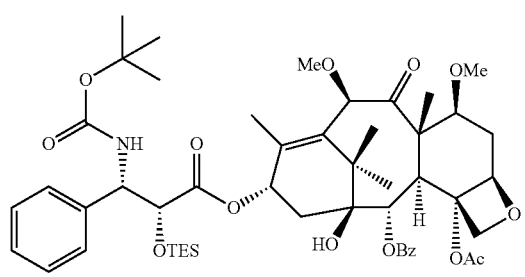

A solution of sodium hydride (60%, 8 eq, 112 mg) was dissolved in 2 mL THF and cooled down to −15° C. under nitrogen. And then 7,10-di-methoxy-10-DAB C1 (1 eq, 200 mg) dissolved in 2 mL THF was added into the sodium hydride mixture. And then was added the mixture of (3R,4S)-tert-butyl-2-oxy-4-phenyl-3-(triethylsilyloxy)azetidine-1-carboxylate (2.5 eq, 329 mg) and LiBr (0.5 eq, 15 mg) in 2 mL THF slowly. The reaction mixture was stirred 2 hours at −15~20° C. until the reaction was complete. The mixture was quenched with 10% AcOH/THF, and extracted with ethylacetate and water. The organic layer was dried by rotavapor to obtain the crude C2 (LC purity: 58%); $^1$H NMR (400 MHz, CDCl$_3$) δ 8.10 (d, J=7.2 Hz, 2H), 7.58 (t, J=7.4 Hz, 1H), 7.47 (t, J=7.6 Hz, 2H), 7.37 (t, J=7.4 Hz, 2H), 7.32-7.27 (m, 3H), 6.29 (t, J=8.6 Hz, 1H), 5.65 (d, J=7.2 Hz, 1H), 5.49 (d, J=9.6 Hz, 1H), 5.27 (d, J=10.0 Hz, 1H), 5.00 (d, J=7.6 Hz, 1H), 4.80 (s, 1H), 4.55 (s, 1H), 4.25 (dd, J=8.4, 52.0 Hz, 2H), 3.94-3.83 (m, 2H), 3.45 (s, 3H), 3.30 (s, 3H), 2.76-2.65 (m, 1H), 2.53 (s, 3H), 2.41-2.14 (m, 2H), 1.95 (s, 3H), 1.85-1.74 (m, 2H), 1.72 (s, 3H), 1.68 (s, 1H), 1.33 (s, 9H), 1.24 (s, 3H), 1.20 (s, 3H), 0.78 (t, J=7.8 Hz, 9H), 0.49-0.28 (m, 6H); $^{13}$C NMR (100 MHz, CDCl$_3$) δ 204.9, 171.7, 170.0, 166.9, 155.2, 139.4, 138.9, 135.0, 133.5, 130.1, 129.2, 128.6, 128.5, 127.7, 126.4, 84.1, 82.4, 81.5, 80.6, 79.8, 78.9, 76.4, 75.2, 74.8, 71.6, 57.2, 57.0, 56.7, 47.2, 43.3, 35.2, 31.9, 28.1, 26.6, 22.9, 21.2, 14.3, 10.3, 6.5, 4.2.

Example 12

Preparation of 1-hydroxy-7β,10β-di-methoxy-9-oxo-5β,20-epoxytax-11-ene-2α,4,13α-triyl4-acetate 2-benzoate 13-{(2R,3S)-3-[(tert-butoxycarbonyl)amino]-2-trethylsilyloxy-3-phenylpropanoate} (C2) by the Catalyst of MgBr$_2$ A solution of sodium hydride (60%, 8 eq, 112 mg) was dissolved in 2 mL THF and cooled down to −15° C. under nitrogen. And then 7,10-di-methoxy-10-DAB C1 (1 eq, 200 mg) dissolved in 2 mL THF was added into the sodium hydride mixture, And then was added the mixture of (3R,4S)-tert-butyl-2-oxy-4-phenyl-3-(triethylsilyloxy)azetidine-1-carboxylate (2.5 eq, 329 mg) and MgBr$_2$ (0.5 eq, 32 mg) in 2 mL THF slowly. The reaction mixture was stirred for 2 hours at −15~20° C. until the reaction was complete. The mixture was quenched with 10% AcOH/THF, and extracted with ethylacetate and water. The organic layer was dried by rotavapor to obtain the crude C2 (LC purity: 79%).

Example 13

Preparation of 1-hydroxy-7β,10β-di-methoxy-9-oxo-5β,20-epoxytax-11-ene-2α,4,13α-triyl4-acetate 2-benzoate 13-{(2R,3S)-3-[(tert-butoxycarbonyl)amino]-2-trethylsilyloxy-3-phenylpropanoate} (C2) by the Catalyst of CsBr A solution of sodium hydride (60%, 8 eq, 112 mg) was dissolved in 2 mL THF and cooled down to −15° C. under nitrogen. And 7,10-di-methoxy-10-DAB C1 (1 eq, 200 mg) dissolved in 2 mL THF was added into the sodium hydride mixture, And then was added the mixture of (3R,4S)-tert-butyl-2-oxy-4-phenyl-3-(triethylsilyloxy)azetidine-1-carboxylate (2.5 eq, 329 mg) and CsBr (0.5 eq, 37 mg) in 2 mL THF slowly. The reaction mixture was stirred for 1.5 hours at −15~20° C. until the reaction was completed. The mixture was quenched with 10% AcOH/THF, and extracted with ethylacetate and water. The organic layer was dried by rotavapor to obtain the crude C2 (LC purity: 85%).

Example 14

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the Catalyst of CeCl$_3$ A solution of sodium hydride (60%, 8 eq, 112 mg) was dissolved in 2 mL THF and cooled down to −15° C. under nitrogen. And then 7,10-di-methoxy-10-DAB C1 (1 eq, 200 mg) dissolved in 2 mL THF was added into the sodium hydride mixture, And then was added the mixture of (3R,4S)-tert-butyl-2-oxy-4-phenyl-3-(triethylsilyloxy)azetidine-1-carboxylate (β-lactam, 2.5 eq, 329 mg) and CeCl$_3$ (0.5 eq, 43 mg) in 2 mL THF slowly. The reaction mixture was stirred for 2.5 hours at −15~20° C. until the reaction was completed. The mixture was quenched with 10% AcOH/THF, and extracted with ethylacetate and water. The organic layer was dried by rotavapor to obtain the crude C2 (LC purity: 87%).

Example 15

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the Catalyst of KBr A solution of sodium hydride (60%, 8 eq, 112 mg) was dissolved in 2 mL THF and cooled down to −15° C. under nitrogen. And then 7,10-di-methoxy-10-DAB C1 (1 eq, 200 mg) dissolved in 2 mL THF was added into the sodium hydride mixture. And then was added the mixture of (3R,4S)-tert-butyl-2-oxy-4-phenyl-3-(triethylsilyloxy)azetidine-1-carboxylate (2.5 eq, 329 mg) and KBr (0.5 eq, 20 mg) in 2 mL THF slowly. The reaction mixture was for stirred 2.5 hours at −15~20° C. until the reaction was completed. The mixture was quenched with 10% AcOH/THF, and extracted with ethylacetate and water. The organic layer was dried by rotavapor to obtain the crude C2 (LC purity: 72%).

Example 16

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the Catalyst of FeCl$_3$ A solution of sodium hydride (60%, 8 eq, 112 mg) was dissolved in 2 mL THF and cooled down to −15° C. under nitrogen. And then 7,10-di-methoxy-10-DAB (1 eq, 200 mg) dissolved in 2 mL THF was added into the sodium hydride mixture, And then was added the mixture of (3R,4S)-tert-butyl-2-oxy-4-phenyl-3-(triethylsilyloxy)azetidine-1-carboxylate (2.5 eq, 329 mg) and FeCl$_3$ (0.5 eq, 28 mg) in 2 mL THF slowly. The reaction mixture was stirred for 2.5 hours at −15~20° C. until the reaction was completed. The mixture was quenched with 10% AcOH/THF, and extracted with ethylacetate and water. The organic layer was dried by rotavapor to obtain the crude C2 (Yield: 45%, LC purity: 95%).

Example 17

Preparation of (1S,2S,3R,4S,7R,9S,10S,12R,15S)-4-(acetyloxy)-15-{[(2R,3S)-3-{[(tert-butoxy)carbonyl]amino}-2-hydroxy-3-phenylpropanoyl]oxy}-1-hydroxy-9,12-dimethoxy-10,14,17,17-tetramethyl-11-oxo-6-oxatetracyclo[11.3.1.0³,¹⁰.0⁴,⁷]heptadec-13-en-2-yl benzoate (Cabazitaxel)

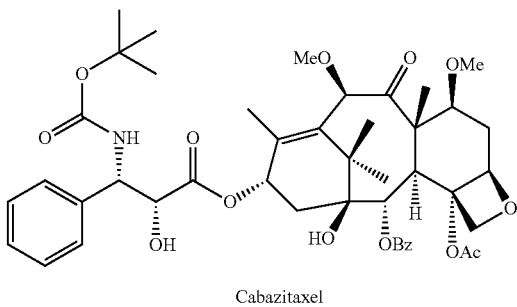

Cabazitaxel

The C2 (490 mg, 1eq) was dissolved in 3.5 mL MeOH and was added dropwise 32% $HCl_{(aq)}$ at −5~5° C., until the pH of C2 mixture reached between 1-2. The reaction mixture was stirred at −5~5° C. until the deprotection was completed, then it was quenched with saturated $NaHCO_{3(aq)}$ and extracted with $CH_2Cl_2$. The organic layer was concentrated and purified by recrystallization ($CH_2Cl_2$/Hexane) at about −18~10° C., about 760 mmHg, for over an hour to yielded cabazitaxel as white solid (yield: 65%; 280 mg, LC purity: 98%). $^1H$ NMR (400 MHz, $CDCl_3$) δ 8.09 (d, J=7.6 Hz, 2H), 7.60 (t, J=7.4 Hz, 1H), 7.48 (t, J=8.0 Hz, 2H), 7.42-7.36 (m, 4H), 7.36-7.29 (m, 1H), 6.20 (t, J=8.6 Hz, 1H), 5.63 (d, J=7.2 Hz, 1H), 5.43 (d, J=9.6 Hz, 1H), 5.26 (d, J=8.8 Hz, 1H), 4.97 (d, J=8.0 Hz, 1H), 4.79 (s, 1H), 4.62 (s, 1H), 4.23 (dd, J=8.2, 50.0 Hz, 2H), 3.90-3.77 (m, 2H), 3.50-3.40 (m, 4H), 3.30 (s, 3H), 2.75-2.64 (m, 1H), 2.36 (s, 3H), 2.32-2.18 (m, 2H), 1.88 (s, 3H), 1.84-1.74 (m, 2H), 1.71 (s, 3H), 1.67 (s, 1H), 1.36 (s, 9H), 1.23-1.17 (m, 6H); $^{13}C$ NMR (100 MHz, $CDCl_3$) δ 204.9, 172.6, 170.3, 166.8, 155.3, 138.7, 138.3, 135.4, 133.6, 130.1, 129.1, 128.7, 128.6, 127.9, 126.7, 84.0, 82.5, 81.6, 80.7, 80.1, 78.6, 76.4, 74.5, 73.7, 72.4, 57.2, 57.0, 56.8, 47.3, 43.2, 35.2, 32.0, 28.1, 26.7, 22.6, 20.6, 14.5, 10.3.

Example 18

Synthesis of Amorphous Cabazitaxel

The cabazitaxel solid (in a crystalline form) of Example 17 was dissolved in dichloromethane (0.6 mL), ethanol (2.0 mL), methanol (0.6 mL), or acetone (0.8 mL), followed by concentration to dryness under reduced pressure (<100 mm Hg) at 40° C. for about 5-10 minutes. The solid obtained was an amorphous form of cabazitaxel, characterized by the analysis in Example 19.

Example 19

Characterization of Amorphous Cabazitaxel

Figure 2:
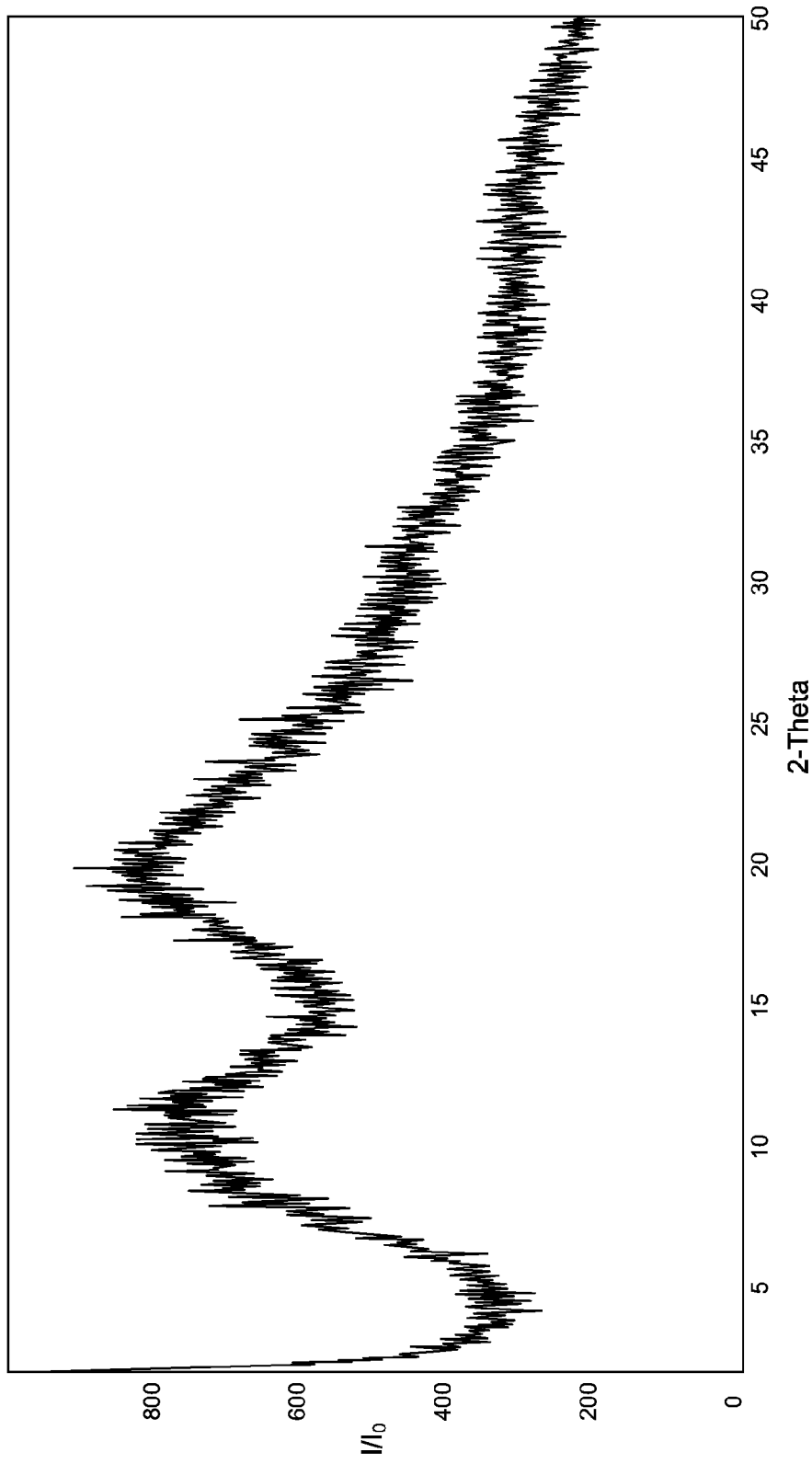
FIG. 2 shows the X-ray powder diffraction pattern of amorphous cabazitaxel (Example 19).
Figure 3:
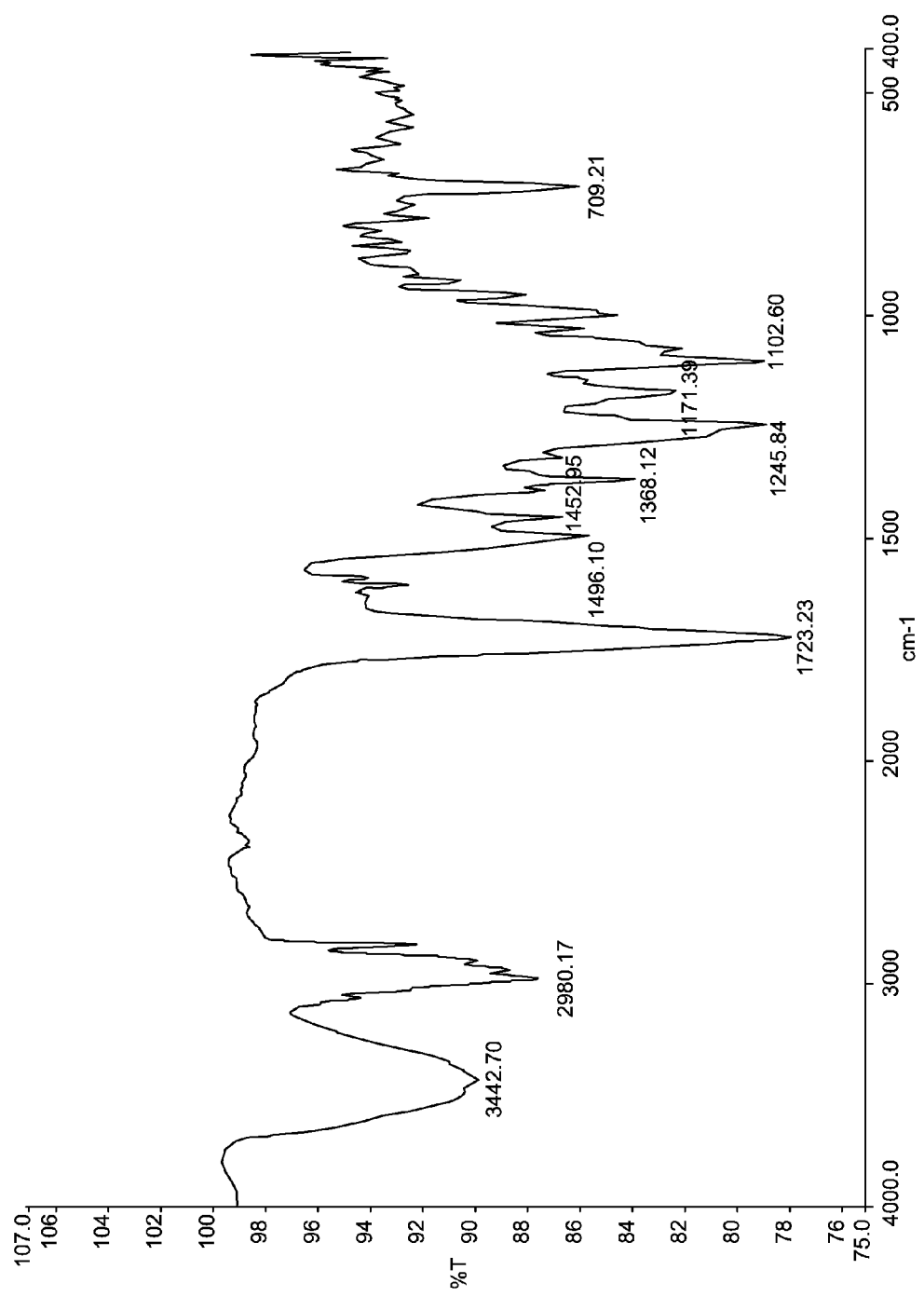
FIG. 3 shows an infrared (IR) spectrum of amorphous cabazitaxel (Example 19).

The amorphous cabazitaxel of Example 18 (prepared by dissolving in ethanol) is identified by the following analyses.
Differential Scanning Calorimetry (DSC) Spectrum
FIG. 1 shows a thermogram of differential scanning calorimetry (DSC) spectrum of the amorphous cabazitaxel. The DSC was run at a heating rate of 10° C./min. There was one endothermal band in the spectrum. The onset temperature was at 143.62° C. and the endothermal maximum of melting is at 145.06° C.
Powder X-Ray Diffraction Analysis
Powder X-ray diffraction (PXRD) analysis of the amorphous cabazitaxel was performed using a SHIMADZU XRD-6000 diffractometer. There was no sharp angel 2θ peak. The PXRD pattern is shown in FIG. 2, where the X-axis is 2-Thera (2θ) and the Y-axis is relative intensity ($I/I_0$).
IR Spectrum
The IR spectrum of the amorphous cabazitaxel was recorded using a Perkin Elmer Spectrum 100. The IR spectrum was shown with absorption bands $v_{max}$ at about 709, 1102, 1171, 1245, 1496, 1723, 2980 and 3442 ($cm^{-1}$) (FIG. 3) The peaks show the special functional groups of cabazitaxel.

While the present invention has been described with reference to the specific embodiments thereof, it should be understood by those skilled in the art that various changes may be made and equivalents may be substituted without departing from the scope of the invention.

What is claimed is:
1. An amorphous form of cabazitaxel characterized by DSC as in FIG. 1 and/or X-ray powder diffraction pattern as in FIG. 2.
2. A pharmaceutical formulation comprising the amorphous form of cabazitaxel of claim 1, and a pharmaceutically acceptable carrier.
3. A process of preparing the amorphous form of cabazitaxel characterized by DSC as in FIG. 1 and/or X-ray powder diffraction pattern as in FIG. 2, comprising:
   dissolving a solid form of cabazitaxel in an organic solvent or an organic solvent mixture, and
   removing the organic solvent or organic solvent mixture within 1-60 minutes to avoid orderly crystal growth and to form the amorphous form of cabazitaxel.
4. The process of claim 3, wherein the solid form is a crystalline form.
5. The process of claim 3, wherein said organic solvent is $C_{1-4}$ halogenated hydrocarbon, $C_{1-4}$ alcohols, $C_{3-5}$ ketone, $C_{1-4}$ nitrile, $C_{2-8}$ ether, or $C_{3-7}$ ester.
6. The process of claim 5, wherein said organic solvent is dichloromethane, ethanol, methanol, or acetone.
7. The process of claim 3, wherein the organic solvent or the organic solvent mixture is removed by evaporation, vacuum condensation, spray drying, or filtration and drying.
8. The process of claim 3, wherein the organic solvent or solvent mixture is removed at 25-60° C. and under a pressure less than about 700 mm Hg.
9. The process of claim 3, wherein the organic solvent or solvent mixture is removed within 3-30 minutes.
10. The process of claim 3, wherein the organic solvent or solvent mixture is removed within 5-10 minutes.

* * * * *